(12) United States Patent
Chang et al.

(10) Patent No.: US 10,975,243 B2
(45) Date of Patent: Apr. 13, 2021

(54) GENETICALLY MODIFIED MICROORGANISM AND METHOD FOR PRODUCING INDIGO DYE

(71) Applicant: INDUSTRIAL TECHNOLOGY RESEARCH INSTITUTE, Hsinchu (TW)

(72) Inventors: Pei-Ching Chang, Zhubei (TW); Jhong-De Lin, Kaohsiung (TW); Chang-Jung Chang, Taoyuan (TW); Ya-Lin Lin, Hsinchu (TW); Hsiang-Yuan Chu, New Taipei (TW); Jie-Len Huang, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 80 days.

(21) Appl. No.: 16/235,088

(22) Filed: Dec. 28, 2018

(65) Prior Publication Data
US 2020/0207988 A1 Jul. 2, 2020

(51) Int. Cl.
*C12N 1/16* (2006.01)
*C12N 1/20* (2006.01)
(Continued)

(52) U.S. Cl.
CPC .............. *C09B 7/02* (2013.01); *C12N 1/16* (2013.01); *C12N 1/20* (2013.01); *C12N 9/0006* (2013.01);
(Continued)

(58) Field of Classification Search
None
See application file for complete search history.

(56) References Cited

U.S. PATENT DOCUMENTS 4,520,103 A    5/1985    Ensley, Jr.
5,173,425 A * 12/1992    Serdar ................ C07K 14/79
                                           435/189
(Continued)

FOREIGN PATENT DOCUMENTS

CN    100413968 C    8/2008
CN    103146596 A    6/2013
(Continued)

OTHER PUBLICATIONS

Berry et al., "Application of metabolic engineering to improve both the production and use of biotech indigo", Journal of Industrial Microbiology and Biotechnology, vol. 28, pp. 127-133, 2002 (Year: 2002).*

(Continued)

*Primary Examiner* — Richard C Ekstrom
(74) *Attorney, Agent, or Firm* — Birch, Stewart, Kolasch & Birch, LLP

(57) ABSTRACT

A genetically modified microorganism includes: an exogenous nucleic acid sequence encoding naphthalene dioxygenase (NDO), wherein the endogenous icd gene of the genetically modified microorganism is knocked out, in which the endogenous icd gene encodes isocitrate dehydrogenase (IDH), and wherein the genetically modified microorganism is capable of using glutamic acid and/or a salt thereof as a nitrogen source to grow and producing indigo dye.

20 Claims, 7 Drawing Sheets

Specification includes a Sequence Listing.

(51) Int. Cl.
*C12N 15/00* (2006.01)
*C09B 7/02* (2006.01)
*C12N 9/02* (2006.01)
*C12N 15/52* (2006.01)
*C12R 1/19* (2006.01)
*C12N 9/04* (2006.01)

(52) U.S. Cl.
CPC .......... *C12N 9/0071* (2013.01); *C12N 15/00* (2013.01); *C12N 15/52* (2013.01); *C12R 1/19* (2013.01); *C12Y 101/01041* (2013.01); *C12Y 114/12012* (2013.01)

(56) References Cited

U.S. PATENT DOCUMENTS

| | | | |
|---|---|---|---|
| 5,496,715 | A | 3/1996 | Goto et al. |
| 5,605,823 | A | 2/1997 | Yen et al. |
| 6,190,892 | B1 | 2/2001 | Weyler et al. |
| 6,849,096 | B2 | 2/2005 | Taguchi et al. |
| 7,960,155 | B1 | 1/2011 | Hauer et al. |
| 2003/0059913 | A1 | 3/2003 | Weyler et al. |
| 2020/0207988 | A1* | 7/2020 | Chang .................. C12R 1/19 |

FOREIGN PATENT DOCUMENTS

| | | |
|---|---|---|
| CN | 103146776 A | 6/2013 |
| CN | 105695336 A | 6/2016 |
| CN | 105802986 A | 7/2016 |
| JP | 8-23988 A | 1/1996 |
| KR | 10-0494764 B1 | 6/2005 |
| KR | 10-0590053 B1 | 6/2006 |
| KR | 10-2011-0065791 A | 6/2011 |
| KR | 10-1190879 B1 | 10/2012 |
| KR | 10-1763243 B1 | 9/2017 |
| KR | 10-1616706 B1 | 1/2018 |
| KR | 10-1850516 B1 | 4/2018 |
| TW | I421342 B | 1/2014 |

OTHER PUBLICATIONS

Taiwanese Office Action and Search Report for Taiwanese Application No. 107147805, dated Jan. 30, 2020.
Xu et al., "Efficient producton of indigoidine in *Escherichia coli*," J Ind Microbiol Biotechnol, vol. 42, 2015 (Published online Jun. 25, 2015), pp. 1149-1155.
Ameria et al., "Characterization of flavin-containing monooxygenase from Corynebacterium glutamicum and its application to production of indigo and indirubin," Biotechnol. Lett., Apr. 8, 2015, 8 pages.
Cheng et al., "Enhancing Indigo Production by Over-Expression of the Styrene Monooxygenase in Pseudomonas putida," Curr. Microbiol., May 6, 2016, 7 pages.
Ensley et al., "Expression of Naphthalene Oxidation Genes in *Escherichia coli* Results in the Biosynthesis of Indigo," Science, vol. 222, Oct. 14, 1983, pp. 167-169.
Han et al., "Bio-indigo production in two different fermentation systems using recombinant *Escherichia coli* cells harboring a flavin-containing monooxygenase gene (fmo)," Process Biochemistry, vol. 46, 2011, pp. 788-791.
Han et al., "Optimization of bio-indigo production by recombinant *E. coli* harboring fmo gene," Enzyme and Microbial Technology, vol. 42, 2008, pp. 617-623.
Lu et al., "Co-expression of P450 BM3 and glucose dehydrogenase by recombinant *Escherichia coli* and its application in an NADPH-dependent indigo production system," J Ind Microbiol Biotechnol, vol. 34, 2007 (published online Dec. 14, 2006), pp. 247-253.
Murdock et al., "Construction of Metabolic Operons Catalyzing the De Novo Biosynthesis of Indigo in *Escherichia coli*," Bio/Technology, vol. 11, Mar. 1993, pp. 381-386.
Pathak et al., "Biosynthesis of Indigo Dye by Newly Isolated Naphthalene-Degrading Strain *Pseudomonas* sp. HOB1 and its Application in Dyeing Cotton Fabric," Appl Biochem Biotechnol, vol. 160, 2010 (published online May 14, 2009), pp. 1616-1626.

* cited by examiner

SEQUENCE LISTING

<160> NUMBER OF SEQ ID NOS: 1

<210> SEQ ID NO 1
<211> LENGTH: 3464
<212> TYPE: DNA
<213> ORGANISM: Pseudomonas putida

<400> SEQUENCE: 1

```
atggaacttc tcatacagcc aaacaatcgc ataattccct tcagtgccgg tgccaacctt      60
ctggaagtgc ttcgcgagaa cggtgtagct atttcctaca gttgcttgtc tgggcgttgc     120
```

```
ggaacctgtc gctgccgggt tatagatggc agtgtcattg attctggggc ggaaaatggg      180
caatcaaacc tcaccgacaa gcagtatgtg ctcgcctgtc agtcagtact cactggcaat      240
tgcgctatcg aagtcccaga agccgacgaa attgtcactc acccggcgcg aatcatcaag      300
ggcacagtgg tcgcagtcga gtcgcccact cacgatatcc gtcgcttacg cgtacgcctc      360
tccaagccct tcgagttctc acccggacag tacgcgacac tgcagttcag ccctgagcat      420
gcgcgtccgt attcaatggc aggtttgcca gatgaccaag aaatggagtt ccacatacgc      480
aaggtgccgg gtgggcgcgt cacggagtat gttttcgaac acgtccgcga aggtacaagc      540
atcaagttga gcgggcctct tggtacggct tatctacgtc agaagcacac cggaccgatg      600
ctgtgtgtag gtggcgggac cggactcgca ccggtgctgt cgattgttcg cggcgcgctg      660
aagtcgggta tgacgaaccc catcctcctt tatttcgggg tgcgcagtca gcaagacctc      720
tacgacgcag agcgattgca caaactcgcc gctgaccacc ctcaactgac cgtacacacg      780
gtgattgcaa cgggcccgat taatgagggt cagcgagccg gcctaattac cgatgtgatc      840
gaaaaagaca tcctttcgct ggctgggtgg agggcctacc tgtgcggcgc accagcgatg      900
gttgaagcgt tgtgcaccgt caccaagcat cttggaatat cacccgaaca tatttatgcc      960
gatgccttct atcccggtgg gatctgaata gttcccggcc atgcacctct gtccatcgag     1020
aattcatcag gaagacattc aaatgaacgt aaacaataag ggcagcgtct gtatttgcgg     1080
cagcgaaatg ctccctaaat tcctcattta ccccatctga ggattgcttt atgacagtaa     1140
agtggattga agcagtcgct ctttctgaca tccttgaagg tgacgtcctc ggcgtgactg     1200
tcgagggcaa ggagctggcg ctgtatgaag ttgaaggcga aatctacgct accgacaacc     1260
tgtgcacgca tggttccgcc cgcatgagtg atggttatct cgagggtaga gaaatcgaat     1320
gccccttgca tcaaggtcgg tttgacgtttt gcacaggcaa agccctgtgc gcacccgtga     1380
cacagaacat caaaacatat ccagtcaaga ttgagaacct gcgcgtaatg attgatttga     1440
gctaagaatt ttaacaggag gcaccccggg ccctagagcg taatcacccc cattccatct     1500
tttttaggtg aaaacatgaa ttacaataat aaaatcttgg taagtgaatc tggtctgagc     1560
caaaagcacc tgattcatgg cgatgaagaa cttttccaac atgaactgaa aaccattttt     1620
gcgcggaact ggcttttctct cactcatgat agcctgattc ctgccccggg cgactatgtt     1680
accgcaaaaa tggggattga cgaggtcatc gtctcccggc agaacgacgg ttcgattcgt     1740
gcttttctga acgtttgccg gcatcgtggc aagacgctgg tgagcgtgga agccggcaat     1800
gccaaaggtt ttgtttgcag ctatcacggc tggggcttcg gctccaacgg tgaactgcag     1860
agcgttccat ttgaaaaaga tctgtacggc gagtcgctca ataaaaaatg tctggggttg     1920
aaagaagtcg ctcgcgtgga gagcttccat ggcttcatct acggttgctt cgaccaggag     1980
gcccctcctc ttatggacta tctgggtgac gctgcttggt acctggaacc tatgttcaag     2040
cattccggcg gtttagaact ggtcggtcct ccaggcaagg ttgtgatcaa ggccaactgg     2100
aaggcacccg cggaaaactt tgtgggagat gcataccacg tgggttggac gcacgcgtct     2160
tcgcttcgct cgggggagtc tatcttctcg tcgctcgctg gcaatgcggc gctaccacct     2220
gaaggcgcag gcttgcaaat gacctccaaa tacggcagcg gcatgggtgt gttgtgggac     2280
ggatattcag gtgtgcatag cgcagacttg gttccggaat tgatggcatt cggaggcgca     2340
aagcaggaaa ggctgaacaa agaaattggc gatgttcgcg ctcggattta tcgcagccac     2400
ctcaactgca ccgtttttccc gaacaacagc atgctgacct gctcgggtgt tttcaaagta     2460
tggaacccga tcgacgcaaa caccaccgag gtctggacct acgccattgt cgaaaaagac     2520
```

```
atgcctgagg atctcaagcg ccgcttggcc gactctgttc agcgaacgtt cgggcctgct    2580
ggcttctggg aaagcgacga caatgacaat atggaaacag cttcgcaaaa cggcaagaaa    2640
tatcaatcaa gagatagtga tctgctttca aaccttggtt tcggtgagga cgtatacggc    2700
gacgcggtct atccaggcgt cgtcggcaaa tcggcgatcg gcgagaccag ttatcgtggt    2760
ttctaccggg cttaccaggc acacgtcagc agctccaact gggctgagtt cgagcatgcc    2820
tctagtactt ggcatactga acttacgaag actactgatc gctaacagac gagtcgacca    2880
tgatgatcaa tattcaagaa gacaagctgg tttccgccca cgacgccgaa gagattcttc    2940
gtttcttcaa ttgccacgac tctgctttgc aacaagaagc cactacgctg ctgacccagg    3000
aagcgcattt gttggacatt caggcttacc gtgcttggtt agagcactgc gtggggtcag    3060
aggtgcaata tcaggtcatt tcacgcgaac tgcgcgcagc ttcagagcgt cgttataagc    3120
tcaatgaagc catgaacgtt tacaacgaaa attttcagca actgaaagtt cgagttgagc    3180
atcaactgga tccgcaaaac tggggcaaca gcccgaagct gcgctttact cgctttatca    3240
ccaacgtcca ggccgcaatg gacgtaaatg acaaagagct acttcacatc cgctccaacg    3300
tcattctgca ccgggcacga cgtggcaatc aggtcgatgt cttctacgcc gcccgggaag    3360
ataaatggaa acgtggcgaa ggtggagtac gaaaattggt ccagcgattc gtcgattacc    3420
cagagcgcat acttcagacg cacaatctga tggtctttct gtga                    3464
```

GENETICALLY MODIFIED MICROORGANISM AND METHOD FOR PRODUCING INDIGO DYE

INCORPORATION BY REFERENCE OF SEQUENCE LISTING

A sequence listing submitted as a text file via EFS-Web is incorporated herein by reference. The text file containing the sequence listing is named "2018-12-28-SequenceListing-0941-3932PUS1.txt"; its date of creation was Dec. 27, 2018; and its size is 4,947 bytes.

TECHNICAL FIELD

The present disclosure relates to the production of indigo dyes, and in particular to genetically modified microorganisms for producing indigo dyes, a method for the preparation thereof, a method for producing indigo dyes, and use of a medium for culturing a genetically modified microorganism and making the genetically modified microorganism produce indigo dye.

BACKGROUND

Indigo dyes can be produced by chemical and biological methods. In the existing chemical production process for indigo dyes, the intermediates produced include formaldehyde and hydrogen cyanide, which are highly polluting. Production of indigo dye by the biological method is through microbial fermentation in which a precursor, such as tryptophan or indole, is converted into indigo dye via an oxygenase. However, it is still difficult for indigo production by biological methods to enter an industrial scale given the current yield.

Glutamic acid (GA) is a widely used seasoning, which is cheap and abundant, but at present, there is no strain or production method that can effectively utilize glutamic acid as a raw material to produce indigo dye.

Therefore, there is need to establish a technology that uses glutamic acid as a raw material using a biological method to produce indigo to reduce the production cost of indigo.

SUMMARY

The present disclosure provides a genetically modified microorganism, comprising: an exogenous nucleic acid sequence encoding naphthalene dioxygenase (NDO), in which the endogenous icd gene of the genetically modified microorganism is knocked out, and the endogenous icd gene encodes isocitrate dehydrogenase (IDH). The genetically modified microorganism mentioned above is capable of using glutamic acid and/or its salts as a nitrogen source to grow and produce indigo dye.

The present disclosure also provides a novel genetically modified strain of *Escherichia coli*, of which the deposit number is DSM 33021. The endogenous icd gene of the novel genetically modified strain of *Escherichia coli* mentioned above is knocked out, and the novel genetically modified strain of *Escherichia coli* mentioned above comprises an exogenous nucleic acid sequence encoding naphthalene dioxygenase.

Furthermore, the present disclosure provides a method for preparing a genetically modified microorganism, comprising the following steps: (a) knocking out the endogenous icd gene of a microorganism to obtain a icd gene-knockout microorganism; (b) performing acclimation on the icd gene-knockout microorganism with a medium containing glutamic acid and/or its salts to obtain an acclimatized microorganism; and (c) introducing an exogenous nucleic acid sequence encoding naphthalene dioxygenase into the acclimatized microorganism to obtain the genetically modified microorganism.

The present disclosure further provides a method for producing indigo dye, comprising the following steps: (a) providing a genetically modified microorganism; and (b) culturing the genetically modified microorganism in a medium containing glutamic acid and/or its salts and a precursor of indigo dye to produce indigo dye. The genetically modified microorganism comprises the genetically modified microorganism mentioned above, a novel genetically modified strain of *Escherichia coli* mentioned above or a genetically modified microorganism prepared by the method for preparing a genetically modified microorganism mentioned above.

The present disclosure further provides a use of a medium for culturing a genetically modified microorganism and producing an indigo dye, in which the medium comprises glutamic acid and/or its salts, and in the medium, the concentration of the glutamic acid and/or its salt is 0.05-80 g/L, and in which the genetically modified microorganism comprises the above exogenous nucleic acid sequence encoding a naphthalene dioxygenase.

A detailed description is given in the following embodiments with reference to the accompanying drawings.

BRIEF DESCRIPTION OF DRAWINGS

The present invention can be more fully understood by reading the subsequent detailed description and examples with references made to the accompanying drawings, wherein.

DETAILED DESCRIPTION

Figure 1A:
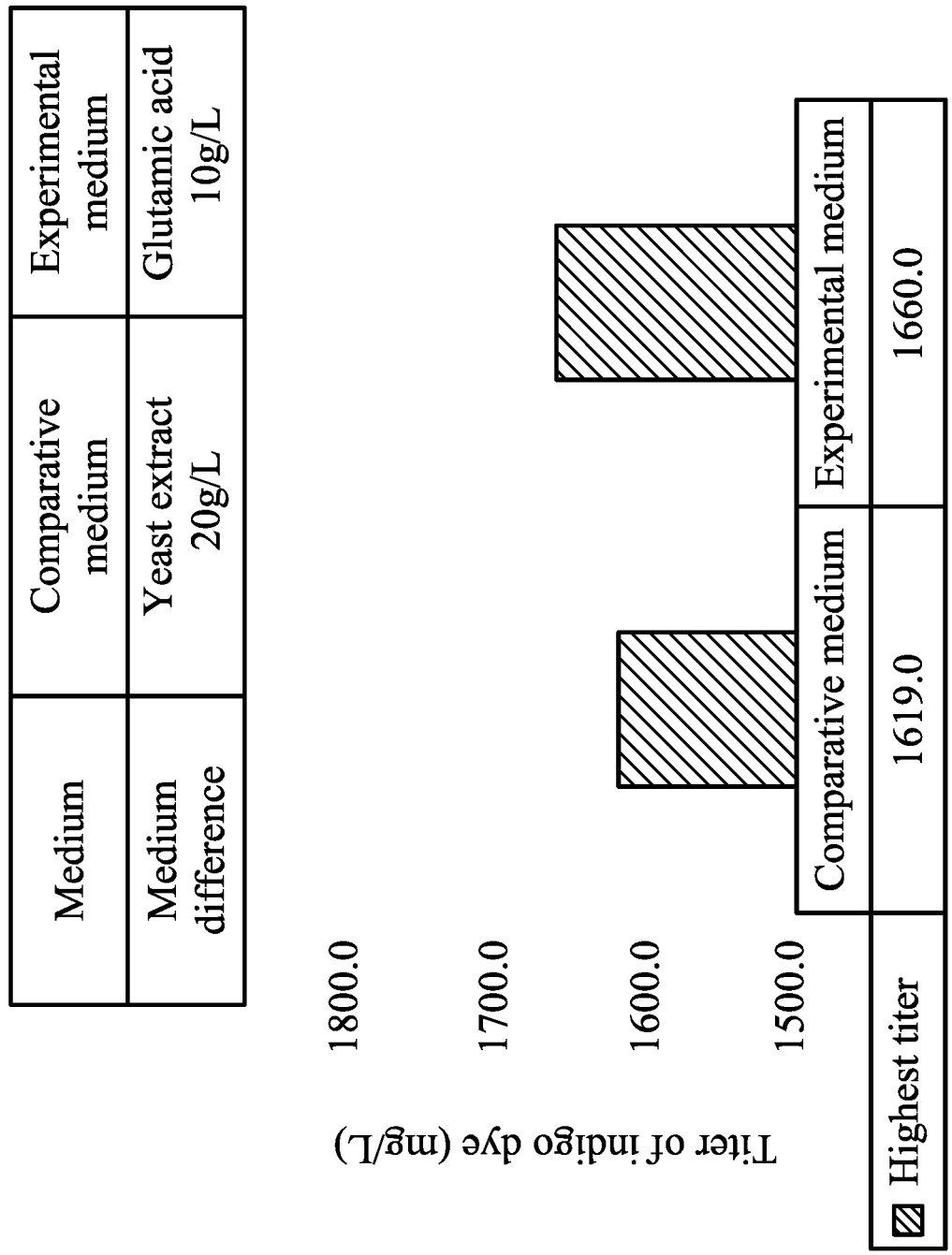
FIG. 1A shows the titers of indigo dye of *Escherichia coli* JD904 cultured in an experimental medium (medium with glutamic acid) and a comparative medium (medium without glutamic acid), respectively.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The present disclosure provides a genetically modified microorganism. The genetically modified microorganism of the present disclosure can be used to produce indigo dye.

The genetically modified microorganism of the present disclosure has the ability to use glutamic acid and/or its salts as a nitrogen source for growth and to produce indigo dye. Due to the low price and sufficient source of glutamic acid, the production cost of the indigo dye can be effectively reduced by the genetically modified microorganism of the present disclosure, which can efficiently utilize glutamic acid and/or its salts.

The microorganism source of the above-mentioned genetically modified microorganisms of the present disclosure may comprise, but is not limited to, a bacterium or a fungus.

Examples of the bacterium of the microorganism source for the genetically modified microorganism of the present disclosure may comprise a bacterium belonging to the genus *Escherichia*, the genus *Enterobacter*, the genus *Enterococcus*, the genus *Lactobacillus*, the genus *Lactococcus*, the genus *Pseudomonas*, the genus *Citrobacter*, the genus *Corynebacterium*, the genus *Erwinia*, the genus *Klebsiella*, the genus *Morganella*, the genus *Pantoea*, the genus *Pectobacterium*, the genus *Proteus*, the genus *Salmonella*, the genus *Serratia*, or the genus *Shigella*, but they are not limited thereto. Examples of a bacterium belonging to the genus *Escherichia* may comprise *Escherichia coli*, but is not limited thereto. Furthermore, the *Escherichia coli* mentioned above may comprise *Escherichia coli* BW25113, K12, DH5α, BL21 or XL1-blue, but is not limited thereto.

In addition, examples of the fungus of the microorganism source for the genetically modified microorganism of the present disclosure may comprise genus *Yarrowia*, the genus *Pichia*, the genus *Rhodotorula*, the genus *Saccharomyces*, the genus *Dekkera*, the genus *Aspergillus*, the genus *Kluyveromyces*, the genus *Penicillium* or the genus *Ustilago*, but they are not limited thereto.

In one embodiment, the microorganism source of the genetically modified microorganism of the present disclosure may be *Escherichia coli*, such as *Escherichia coli* BW25113.

In one embodiment, the genetically modified microorganism of the present disclosure may comprise an exogenous nucleic acid sequence encoding naphthalene dioxygenase (NDO), but it is not limited thereto.

The foregoing exogenous nucleic acid sequence encoding naphthalene dioxygenase may be any sequence as long as the protein encoded thereby has the effect of naphthalene dioxygenase. For example, the exogenous nucleic acid sequence may comprise a sequence having at least 85% sequence identity to the sequence of SEQ ID NO. 1, but it is not limited thereto. In one embodiment, the foregoing exogenous nucleic acid sequence may comprise the sequence of SEQ ID NO. 1. In another embodiment, the foregoing exogenous nucleic acid sequence may be the sequence of SEQ ID NO. 1.

Moreover, icd gene is a gene encoding isocitrate dehydrogenase (IDH) in a tricarboxylic acid cycle (TCA). If isocitrate dehydrogenase does not work in the tricarboxylic acid cycle, more glutamic acid can enter the nitrogen cycle, thereby improving the efficiency of using glutamic acid as a nitrogen source by a microorganism. Therefore, for the genetically modified microorganism of the present disclosure, in addition to it may comprise the exogenous nucleic acid sequence encoding the naphthalene dioxygenase, the endogenous icd gene thereof may be further knocked out to further promote the utilization efficiency of the glutamic acid by the microorganism.

In one specific embodiment, the genetically modified microorganism of the present invention mentioned above may be a genetically modified strain of *Escherichia coli*, JD938, deposited in Leibniz Institute Deutsche Sammlung von Mikroorganismen and Zelkulturen GmbH (DSMZ) of German Collection of Microorganisms and Cell Cultures on Feb. 6, 2019, of which the deposit number is DSM 33021. The deposit will be maintained under the terms of the Budapest Treaty. This deposit is not an admission that a deposit is required under 35 U.S.C. § 112. The deposit will irrevocably and without restriction or condition be available to the public upon issuance of a patent. However, it should be understood that the availability of a deposit does not constitute a license to practice the subject invention in derogation of patent rights granted by government action.

The present disclosure also provides a novel genetically modified strain of *Escherichia coli*, which is a genetically modified strain of *Escherichia coli*, JD938, deposited in Leibniz Institute Deutsche Sammlung von Mikroorganismen und Zelkulturen GmbH (DSMZ) of German Collection of Microorganisms and Cell Cultures on Feb. 6, 2019, of which the deposit number is DSM 33021.

The present disclosure also provides a method for preparing a genetically modified microorganism, which may comprise the following steps, but it is not limited thereto.

First, the endogenous icd gene of a microorganism is knocked out to obtain an icd gene-knockout microorganism.

The method for knocking out the endogenous icd gene of the microorganism mentioned above is not particularly limited as long as the endogenous icd gene can be inactivated without affecting the performance of non-target genes. For example, it can be performed by any method known in the art that knocks out the endogenous target genes, such as homologous recombination, phage transduction, Clustered Regularly Interspaced Short Palindromic Repeats-Cysteine asparate protease (Caspase) 9 (CRISPER-Cas9 system), etc., but they are not limited thereto.

The microorganism mentioned above may comprise, but is not limited to, a bacterium or a fungus.

Examples and descriptions of the above-mentioned bacterium may be the same as those of the bacterium described in the paragraphs related to the above-described genetically modified microorganism of the present disclosure, and thus will not be repeated herein to prevent redundancy.

Similarly, examples and descriptions of the above-mentioned fungus may be the same as those of the fungus described in the paragraphs related to the above-described genetically modified microorganism of the present disclosure, and thus thereof will not be repeated herein to prevent redundancy.

Next, acclimation is performed on the icd gene-knockout microorganism with a medium containing glutamic acid and/or its salts to obtain an acclimatized microorganism, and the glutamic acid utilization rate of the above-mentioned acclimatized microorganism may be higher than that of the above-mentioned icd gene-knockout microorganism. In this medium, the concentration of glutamic acid and/or its salts may be about 0.05-80 g/L, such as about 0.1-80 g/L, about 0.1-70 g/L, about 0.1-60 g/L, about 0.5-55 g/L, about 0.5-40 g/L, about 1-50 g/L, about 1-30 g/L, about 5-20 g/L, about 10-30 g/L, about 15-40 g/L, about 5-45 g/L, but is not limited thereto.

In one embodiment, the foregoing medium containing glutamic acid and/or its salts may further comprise an M9 salt solution.

The M9 salt solution comprises $Na_2HPO_4.2H_2O$, $KH_2PO_4$, NaCl and $NH_4Cl$. The foregoing M9 salt solution may be a 1-fold (1×) M9 salt solution, but is not limited thereto. In a 1-fold (1×) M9 salt solution, the concentration of $Na_2HPO_4.2H_2O$ is about 7.52 g/L, the concentration of $KH_2PO_4$ is about 3.0 g/L, the concentration of NaCl is about 0.5 g/L, and the concentration of $NH_4Cl$ is about 0.5 g/L.

Moreover, in one embodiment, the foregoing medium containing glutamic acid and/or its salts may further comprise a carbon source. The kind of carbon source is not particularly limited as long as it can be used as a carbon source by the microorganism to be cultured, such as glycerol, glucose, lactose, etc., but is not limited thereto. In the foregoing medium containing glutamic acid and/or its salts, the concentration of the carbon source may be about 0.05-100 g/L, such as about 0.05-15 g/L, 0.1-20 g/L, 0.5-15 g/L, 1-10 g/L, 5-20 g/L, 5-30 g/L, 10-50 g/L, 20-60 g/L, 20-80 g/L, 30-100 g/L, but is not limited thereto. In one specific embodiment, the carbon source mentioned above is glycerol, and in the foregoing medium containing glutamic acid and/or its salts, the concentration of the glycerol may be about 0.05-80 g/L, such as about 0.05-15 g/L, 0.1-20 g/L, 0.5-15 g/L, 1-10 g/L, 1-20 g/L, 1-30 g/L, 5-40 g/L, 5-50 g/L, 10-60 g/L, 15-70 g/L, 20-80 g/L.

In one embodiment, the above-mentioned acclimation performed on the icd gene-knockout microorganism with a medium containing glutamic acid and/or its salts, may comprise, but is not limited to performing a first concentration culturing. In the first concentration culturing, the icd gene-knockout microorganism is cultured with a medium containing a first concentration of glutamic acid and/or its salts to a stationary phase. The first concentration of the glutamic acid and/or its salts mentioned above in the medium may be about 0.05-80 g/L, such as about 0.1-80 g/L, about 0.1-70 g/L, about 0.1-60 g/L, about 0.5-55 g/L, about 0.5-40 g/L, about 1-50 g/L, about 1-30 g/L, about 5-20 g/L, about 10-30 g/L, about 15-40 g/L, about 5-45 g/L, but it is not limited thereto. In one embodiment, in the medium containing glutamic acid and/or its salts mentioned above, the concentration of the glutamic acid and/or its salts may be about 1 g/L, 5 g/L, and 10 g/L, 15 g/L, 20 g/L, 30 g/L, 40 g/L, 50 g/L, 60 g/L, 70 g/L or 80 g/L, but is not limited thereto. Furthermore, depending on needs, the first concentration culturing may be performed in only one cycle, or the first concentration culturing may be performed in plural cycles, and it is not particularly limited. In one specific embodiment, the first concentration culturing may be performed in 3-6 cycles, but is not limited thereto, and the operator may adjust the number of cycles according to actual conditions.

Moreover, in the first concentration culturing mentioned above, the time for culturing the microorganism to a stationary phase depends on the type of the microorganism, the culturing conditions, and the like, and is not particularly limited. For example, in the first concentration culturing mentioned above, the microorganism may be cultured for about 12-84 hours, such as about 12-24 hours, about 36-48 hours, about 48-60 hours, about 60-72 hours, about 24 hours, about 48 hours, about 72 hours, to a stationary phase, but it is not limited thereto.

In addition, in the first concentration culturing, the temperature for culturing the microorganism also depends on the kind of microorganism, the culturing conditions, and the like, and is not particularly limited. For example, in the first concentration culturing mentioned above, the microorganism can be cultured at about 25-40° C., such as about 25-30° C., about 30-35° C., about 30-40° C., about 28° C., about 30° C., about 32° C., about 37° C., about 40° C., but it is not limited thereto.

In another embodiment, the foregoing acclimation performed on the icd gene-knockout microorganism with a medium containing glutamic acid and/or its salts, in addition to the first concentration culturing mentioned above, may further comprise, but is not limited to, after the first concentration culturing, performing at least one round of an increased concentration culturing, and in each round of the increased concentration culturing, culturing the icd gene-knockout microorganism in a medium containing glutamic acid and/or its salts at a higher concentration than the first concentration to the stationary phase. Moreover, the concentration of glutamic acid and/or its salts in the medium used for each round of the increased concentration culturing is higher than that of the previous round.

Furthermore, the number of the at least one round of the increased concentration culturing is not particularly limited, and may depend on the physiological condition of the microorganism, such as the utilization efficiency of glutamic acid. For example, if the utilization of glutamic acid of the microorganism is low or less than the expectation, then the increased concentration culturing can be continued. Conversely, if the utilization of glutamic acid of the microorganism is high or has reached the expectation, then the subsequent increased concentration culturing can be stopped. In one embodiment, after the first concentration culturing, about 1-5 rounds of the increased concentration culturing may be performed, for example, 3 rounds of the increased concentration culturing may be sequentially performed, but it is not limited thereto.

Moreover, each round of the above-mentioned increased concentration culturing independently depends as needed. The increased concentration culturing in each round may be performed in only one cycle, or it may be performed in plural cycles, and it is not particularly limited. In one specific embodiment, the above-mentioned increased concentration culturing in each round can be independently performed in about 3-6 cycles, but it is not limited thereto, and the operator can adjust the number of cycles according to actual conditions.

Furthermore, in the method for preparing a genetically modified microorganism mentioned above, after performing acclimation on the foregoing icd gene-knockout microorganism with a medium containing glutamic acid and/or its salts to obtain an acclimatized microorganism, an exogenous nucleic acid sequence encoding naphthalene dioxygenase is introduced into the acclimatized microorganism mentioned above to obtain the genetically modified microorganism for producing indigo dye.

The manner for introducing the exogenous nucleic acid sequence encoding naphthalene dioxygenase mentioned above into the acclimatized microorganism is not particularly limited as long as the exogenous nucleic acid sequence can be introduced into the above-mentioned acclimatized microorganism and can be expressed. For example, the foregoing exogenous nucleic acid sequence can be introduced into the above-mentioned acclimatized microorganism via a vector, but is not limited thereto. Moreover, the kind of vector mentioned above depends on the type of vector for which the microorganism to be actually used is suitable. For example, a specific plasmid may be used as a vector, but is not limited thereto. In addition, the exogenous nucleic acid sequence can be introduced into the genome of the strain to make it be expressed. In one embodiment, the foregoing exogenous nucleic acid sequence can be introduced into the foregoing acclimatized microorganism via a plasmid.

The foregoing exogenous nucleic acid sequence may comprise a sequence having at least 85% sequence identity to the sequence of SEQ ID NO. 1, but it is not limited thereto. In one embodiment, the foregoing exogenous nucleic acid sequence may comprise the sequence of SEQ ID NO. 1. In another embodiment, the foregoing exogenous nucleic acid sequence may be the sequence of SEQ ID NO. 1.

In one specific embodiment, in the method for preparing a genetically modified microorganism of the present disclosure mentioned above, the said genetically modified microorganism may be a genetically modified *Escherichia coli* deposited in Leibniz Institute Deutsche Sammlung von Mikroorganismen and Zelkulturen GmbH (DSMZ) of German Collection of Microorganisms and Cell Cultures on Feb. 6, 2019, of which the deposit number is DSM 33021.

In addition, according to the foregoing, the present disclosure can further provide any genetically modified microorganism prepared by any method for preparing a genetically modified microorganism of the present disclosure mentioned above.

In one embodiment, any genetically modified microorganism prepared by any method for preparing a genetically modified microorganism of the present disclosure mentioned above may be used to produce indigo dye, but it is not limited thereto.

Furthermore, the present disclosure may also provide a method for producing indigo dye.

The method for producing indigo dye of the present disclosure may comprise the following steps, but it is not limited thereto.

In the method for producing indigo dye of the present disclosure, a genetically modified microorganism can be cultured in a medium containing glutamic acid and/or its salts and a precursor of indigo dye to make the genetically modified microorganism mentioned above grow by using the above glutamic acid and/or its salts as a nitrogen source and to use the precursor of indigo dye as a substrate to produce indigo dye.

Examples of the genetically modified microorganism containing exogenous nucleic acid sequence mentioned above may comprise, but is not limited to, any genetically modified microorganism of the present disclosure mentioned above, the novel genetically modified strain of *Escherichia coli* of the present disclosure mentioned above or any genetically modified microorganism prepared by any method for preparing a genetically modified microorganism of the present disclosure mentioned above.

Furthermore, in the foregoing medium containing glutamic acid and/or its salts and a precursor of indigo dye, the concentration of glutamic acid and/or its salts may be about 0.05-80 g/L, such as about 0.1-80 g/L, about 0.1-70 g/L, about 0.1-60 g/L, about 0.5-55 g/L, about 0.5-40 g/L, about 1-50 g/L, about 1-30 g/L, about 5-20 g/L, about 10-30 g/L, about 15-40 g/L, about 5-45 g/L, etc., but it not limited thereto. In one embodiment, in the foregoing medium containing glutamic acid and/or its salts and a precursor of indigo dye, the concentration of glutamic acid and/or its salts may be about 1 g/L, 5 g/L, 10 g/L, 15 g/L, 20 g/L, 30 g/L, 40 g/L, 50 g/L, 60 g/L, 70 g/L or 80 g/L.

Examples of the above precursor of indigo dye may comprise, but are not limited to, tryptophan, indole, and the like. Furthermore, the concentration of the precursor of indigo dye in the foregoing medium containing glutamic acid and/or its salts and a precursor of indigo dye may be about 0.1-25 g/L, such as about 0.5-20 g/L, about 1-15 g/L, about 2-12 g/L. In one embodiment, the concentration of the precursor of indigo dye may be about 3-10 g/L. In one embodiment, the precursor of indigo dye may be tryptophan, and in the foregoing medium containing glutamic acid and/or its salt and a precursor of indigo dye, the concentration of tryptophan may be about 0.1-25 g/L, such as about 0.1-20 g/L, about 1-20 g/L, about 2-18 g/L, about 3-15 g/L, about 3-10 g/L, about 5-15 g/L, but is not limited thereto.

In one embodiment, the foregoing medium containing glutamic acid and/or its salt and a precursor of indigo dye may further comprise a yeast extract. The concentration of the yeast extract in the foregoing medium containing glutamic acid and/or its salt and a precursor of indigo dye may be about 0.05-30 g/L, such as about 0.1-30 g/L, about 0.5-25 g/L, about 1-20 g/L, about 2-18 g/L, about 3-15 g/L, about 3-10 g/L, about 5-20 g/L, but it is not limited thereto. In one embodiment, the concentration of yeast extract in the foregoing medium containing glutamic acid and/or its salt and a precursor of indigo dye may be about 1 g/L, 3 g/L, 5 g/L, 20 g/L or 30 g/L.

In another embodiment, the foregoing medium containing glutamic acid and/or its salt and a precursor of indigo dye may further comprise a M9 salt solution, thiamine, glycerol, $CaCl_2$, $MgSO_4$ and isopropyl β-D-1-thiogalactopyranoside (IPTG).

The M9 salt solution comprises $Na_2HPO_4 \cdot 2H_2O$, $KH_2PO_4$, NaCl, and $NH_4Cl$. The M9 salt solution mentioned above may be a 1-fold (1×) M9 salt solution, but it is not limited thereto. In a 1-fold (1×) M9 salt solution, the concentration of $Na_2HPO_4 \cdot 2H_2O$ is about 7.52 g/L, the concentration of $KH_2PO_4$ is about 3.0 g/L, the concentration of NaCl is about 0.5 g/L, and the concentration of $NH_4Cl$ is about 0.5 g/L.

Furthermore, the concentration of thiamine in the foregoing medium containing glutamic acid and/or its salt and a precursor of indigo dye may be about 0.05-20 mg/L, such as about 0.05-10 mg/L, or about 0.1-15 mg/L, about 0.1-1 mg/L, about 0.5-8 mg/L, about 1-5 mg/L, but it is not limited thereto. The concentration of glycerol in the foregoing medium containing glutamic acid and/or its salt and a precursor of indigo dye may be about 0.05-80 g/L, such as about 0.05-15 g/L, 0.1-20 g/L, 0.5-15 g/L, 1-10 g/L, 1-20 g/L, 1-30 g/L, 5-40 g/L, 5-50 g/L, 10-60 g/L, 15-70 g/L, 20-80 g/L, but it is not limited thereto. The concentration of $MgSO_4$ in the foregoing medium containing glutamic acid and/or its salt and a precursor of indigo dye may be about 0.05-20 mM, such as about 0.05-10 mM, about 0.1-15 mM, about 0.1-1 mM, about 0.5-8 mM, about 1-5 mM, but it is not limited thereto. Moreover, the concentration of $CaCl_2$ in the foregoing medium containing glutamic acid and/or its salt and a precursor of indigo dye may be about 0.05-20 μM, such as about 0.05-10 μM, about 0.1-15 μM, about 0.1-10 μM, about 0.5-8 μM, about 1-5 μM, but it is not limited thereto. The concentration of isopropyl-β-D-thiogalactoside in the foregoing medium containing glutamic acid and/or its salt and a precursor of indigo dye may be about 0.005-10 mM, such as about 0.005-5 mM, about 0.01-10 mM, about 0.01-1 mM, about 0.1-10 mM, about 0.1-5 mM, about 0.5-5 mM, but it is not limited thereto.

In still another embodiment, the foregoing medium containing glutamic acid and/or its salt and a precursor of indigo dye, in addition to an M9 salt solution, thiamine, glycerol, $CaCl_2$, $MgSO_4$ and isopropyl-β-D-thiogalactopyranoside (IPTG), may further comprise a yeast extract. The concentration of the yeast extract in the foregoing medium containing glutamic acid and/or its salt and a precursor of indigo dye may be about 0.05-30 g/L, such as about 0.1-30 g/L, about 0.5-25 g/L, about 1-20 g/L, about 2-18 g/L, about 3-15 g/L, about 3-10 g/L, about 5-20 g/L, but it is not limited thereto. In one embodiment, the concentration of the yeast extract in the foregoing medium containing glutamic acid and/or its salt and a precursor of indigo dye may be about 1 g/L, 3 g/L, 5 g/L or 20 g/L.

Furthermore, in the method for producing indigo dye of the present disclosure, the time for culturing the above-mentioned genetically modified microorganism depends on the kind of microorganism, the culturing conditions, and the like, and is not particularly limited. For example, the genetically modified microorganism mentioned above can be cultured for about 12-84 hours, such as about 12-24 hours, about 36-48 hours, about 48-60 hours, about 60-72 hours, about 24 hours, about 48. Hours, about 72 hours, to a stationary phase, but it is not limited thereto.

In addition, in the method for producing indigo dye of the present disclosure, the temperature for culturing the above-described genetically modified microorganism also depends on the kind of microorganism, the culturing conditions, and the like, and is not particularly limited. For example, in the method for producing indigo dye of the present disclosure, the microorganism can be cultured at about 25-40° C., such as about 25-30° C., about 30-35° C., about 30-40° C., about 28° C., about 30° C., about 32° C., about 37° C., about 40° C., but it is not limited thereto.

By any method for producing indigo dye of the present disclosure mentioned above, not only enable the microorganism to effectively utilize glutamic acid, but also effectively increases the production efficiency of the indigo dye of the cells and the content of the indigo dye in the cells.

The present disclosure also provides a use of a medium for culturing a genetically modified microorganism and making the genetically modified microorganism produce indigo dye.

The foregoing medium may comprise glutamic acid and/or its salts, but it is not limited thereto. The concentration of glutamic acid and/or its salts in the foregoing medium may be about 0.05-60 g/L, such as about 0.1-60 g/L, about 0.5-55 g/L, about 0.5-40 g/L, about 1-50 g/L, about 1-30 g/L, about 5-20 g/L, about 10-30 g/L, about 15-40 g/L, about 5-45 g/L, but it is not limited thereto. In one embodiment, the concentration of glutamic acid and/or its salts in the foregoing medium may be about 1 g/L, 5 g/L, 10 g/L, 15 g/L, 20 g/L, 30 g/L, 40 g/L or 50 g/L.

The foregoing medium, in addition to glutamic acid and/or its salts, may further comprise a precursor of indigo dye. Examples of the foregoing precursor of indigo dye may comprise, but are not limited to, tryptophan, indole, and the like. Furthermore, the concentration of the precursor of indigo dye in the foregoing medium may be about 0.1-25 g/L, such as about 0.5-20 g/L, about 1-15 g/L, about 2-12 g/L, or the like. In one embodiment, the concentration of the precursor of indigo dye may be about 3-10 g/L. In one embodiment, the precursor of indigo dye is tryptophan, and in the foregoing medium, the concentration of tryptophan may be about 0.1-25 g/L, such as about 0.1-20 g/L, about 1-20 g/L, about 2-18 g/L, about 3-15 g/L, about 3-10 g/L, about 5-15 g/L, but it is not limited thereto.

The foregoing medium may further comprise a carbon source. The kind of carbon source is not particularly limited as long as it can be used as a carbon source by the microorganism to be cultured, such as glycerol, glucose, lactose, but it is not limited thereto. In the foregoing medium, the concentration of the carbon source may be about 0.05-100 g/L, such as about 0.05-15 g/L, 0.1-20 g/L, 0.5-15 g/L, 1-10 g/L, 5-20 g/L, 5-30 g/L, 10-50 g/L, 20-60 g/L, 20-80 g/L, 30-100 g/L, but it is not limited thereto. In a specific embodiment, the carbon source is glycerol, and the concentration of glycerol in the foregoing medium may be about 0.05-80 g/L, such as about 0.05-15 g/L, 0.1-20 g/L, 0.5-15 g/L, 1-10 g/L, 1-20 g/L, 1-30 g/L, 5-40 g/L, 5-50 g/L, 10-60 g/L, 15-70 g/L, 20-80 g/L, but it is not limited thereto.

Moreover, in one embodiment, the foregoing medium may further comprise a yeast extract in addition to glutamic acid and/or its salts. The concentration of the yeast extract in the foregoing medium may be about 0.05-30 g/L, such as about 0.1-30 g/L, about 0.5-25 g/L, about 1-20 g/L, about 2-18 g/L, about 3-15 g/L, about 3-10 g/L, about 5-20 g/L, but it is not limited thereto. In one specific embodiment, the concentration of the yeast extract in the foregoing medium may be about 1 g/L, 3 g/L, 5 g/L or 20 g/L.

In another embodiment, the foregoing medium in addition to glutamic acid and/or its salts may further comprise a M9 salt solution, thiamine, glycerol, $CaCl_2$, $MgSO_4$, and isopropyl-β-D-thiogalactoside.

The descriptions related to the M9 salt solution and its components may be the same as those of the M9 salt solution recited in the paragraphs related to the above-described method for producing indigo dye of the present disclosure, and thus will not be repeated herein to prevent redundancy.

Similarly, the descriptions related to the concentrations of thiamine, glycerol, $CaCl_2$, $MgSO_4$ and isopropyl-β-D-thiogalactoside may be the same as those of thiamine, glycerol, $CaCl_2$, $MgSO_4$ and isopropyl-β-D-thiogalactoside recited in the paragraphs related to the above-described method for producing indigo dye of the present disclosure, and thus will not be repeated herein to prevent redundancy.

Moreover, in still another embodiment, the foregoing medium, in addition to glutamic acid and/or its salts, a M9 salt solution, thiamine, glycerol, CaCl2, MgSO4 and isopropyl-β-D-thiogalactoside, may further comprise a yeast extract. The concentration of the yeast extract in the foregoing medium may be about 0.05-30 g/L, such as about 0.1-30 g/L, about 0.5-25 g/L, about 1-20 g/L, about 2-18 g/L, about 3-15 g/L, about 3-10 g/L, about 5-20 g/L, but it is not limited thereto. In one embodiment, the concentration of the yeast extract in the foregoing medium may be about 1 g/L, 3 g/L, 5 g/L or 20 g/L.

Moreover, in the use of a medium for culturing a genetically modified microorganism and making the genetically modified microorganism produce indigo dye, the genetically modified microorganism may comprise, but is not limited to, an exogenous nucleic acid sequence encoding naphthalene dioxygenase.

The exogenous nucleic acid sequence mentioned above may comprise a sequence having at least 85% sequence identity to the sequence of SEQ ID NO. 1, but it is not limited thereto. In one embodiment, the exogenous nucleic acid sequence mentioned above may comprise the sequence of SEQ ID NO. 1. In another embodiment, the exogenous nucleic acid sequence mentioned above may be the sequence of SEQ ID NO. 1.

Moreover, in the use of a medium for culturing a genetically modified microorganism and making the genetically modified microorganism produce indigo dye of the present disclosure, for the genetically modified microorganism mentioned above, in addition to it may comprise the exogenous nucleic acid sequence encoding the naphthalene dioxygenase, the endogenous icd gene thereof may be further knocked out.

Furthermore, in one specific embodiment, in the use of a medium for culturing a genetically modified microorganism and making the genetically modified microorganism produce indigo dye of the present disclosure, the said microorganism may be any genetically modified microorganism of the present disclosure mentioned above, the novel genetically modified strain of *Escherichia coli* of the present disclosure mentioned above or any genetically modified microorganism prepared by any method for preparing a genetically modified microorganism of the present disclosure mentioned above.

In the use of the medium of the present invention for culturing a genetically modified microorganism and producing an indigo dye in the use of a medium for culturing a genetically modified microorganism and making the genetically modified microorganism produce indigo dye of the present disclosure, the said medium has the effect of enabling the microorganism to effectively utilize glutamic acid and effectively increase the titer of the indigo dye.

EXAMPLES

1. Example 1

1.1 Genetic Modification for Bacterial Strains

*Escherichia coli* BW25113 was used as a source strain for genetic modification to prepare the respective strains shown in Table 1.

TABLE 1

| Name | Description |
|---|---|
| Plasmid | |
| JDBP00 | PLlacO1::NDO; ColE1 ori; KanR |
| Strain | |
| *Escherichia coli* BW25113 | (rrnBT14 ΔlacZWJ16 hsdR514 ΔaraBADAH33 ΔrhaBADLD78) |
| *Escherichia coli* JDG0 | (rrnBT14 ΔlacZWJ16 hsdR514 ΔaraBADAH33 ΔrhaBADLD78 Δicd) |
| *Escherichia coli* JDG1 | JDG0 acclimated by glutamic acid with different concentrations |
| *Escherichia coli* JDG2 | |
| *Escherichia coli* JDG3 | |
| *Escherichia coli* JDG4 | |
| *Escherichia coli* JD938 | JDG4 to which the plasmid JDBP00 is introduced |

1.1.1 Preparation of *Escherichia coli* JDG0 (Endogenous Icd Gene-Knockout *Escherichia coli* BW25113)

The endogenous icd gene of *Escherichia coli* BW25113 was knocked out by the method of a one-step inactivation of chromosome gene recited in Proc Natl Acad Sci USA. 2000 Jun. 6; 97(12):6640-5. In this method, the icd gene on the chromosome of *Escherichia coli* BW25113 was knocked out by a primer complementary to the sequence of the icd gene on the chromosome via homologous recombination.

Next, the icd gene-knockout *Escherichia coli* BW25113 could be confirmed by a polymerase chain reaction. *Escherichia coli* BW25113, which had been confirmed that no icd gene on the chromosome, was identified as *Escherichia coli* JDG0.

1.2 Preparation of Acclimatized *Escherichia coli*

The obtained *Escherichia coli* JDG0 was acclimatized by a manner in which the concentration of glutamic acid in the medium was gradually increased (1 g/L to 10 g/L). The medium used was M9 (minimum medium) medium. The formulation of the M9 medium is as shown in Table 2, and 10 g/L of glycerol was added as a carbon source to the M9 medium.

TABLE 2

| M9 slats | | |
|---|---|---|
| KH$_2$PO$_4$ | 1.5 | g/L |
| Na$_2$HPO$_4$ | 3.39 | g/L |
| NaCl | 0.25 | g/L |
| NH$_4$Cl | 0.5 | g/L |

A single colony of *Escherichia coli* JDG0 was inoculated into a shake flask and cultured at 37° C. After 72 hours of culture, an appropriate amount of the bacterial suspension was applied to a plating medium with an initial glutamic acid concentration, and cultured at 37° C. for 48-72 hours. The medium with the initial glutamic acid concentration was used to perform in 3-6 cycles. Thereafter, a large colony was picked for the next round of culturing with a higher glutamate concentration, and 3-6 cycles of culturing was carried out in the next round, similarly. The strain was cultured by gradually increasing the concentration of glutamic acid in the manner mentioned above.

In each round of culturing with different glutamic acid concentrations, a bacterial strain was selected. The selected strains based on the glutamic acid culturing concentrations from low to high were *Escherichia coli* JDG1, *Escherichia coli* JDG2, *Escherichia coli* JDG3 and *Escherichia coli* JDG4, respectively.

*Escherichia coli* JDG0, *Escherichia coli* JDG1, *Escherichia coli* JDG2, *Escherichia coli* JDG3 and *Escherichia coli* JDG4 were analyzed for glutamic acid consumption rate. The results are as shown in Table 3.

TABLE 3

| | Growth of strain (OD$_{600}$) | Glutamic acid consumption rate (mg/hour) |
|---|---|---|
| Strain before acclimation, JDG0 | 1.0 | 0.8 |
| Acclimatized strain, JDG1 | 1.2 | 8.3 |
| Acclimatized strain, JDG2 | 2.4 | 14.8 |
| Acclimatized train, JDG3 | 9.8 | 33.3 |
| Acclimatized strain, JDG4 | 16.3 | 204.4 |

According to Table 3, it is known that *Escherichia coli* JDG4 has the highest consumption rate of glutamic acid.

1.3 Preparation of Strain Expressing Naphthalene Dioxygenase (NDO)

A plasmid DNA capable of expressing a gene of naphthalene dioxygenase (NDO) (the source species of which was *Pseudomonas putida* and whose sequence was the sequence of SEQ ID NO. 1) (JDBP00) was introduced into *Escherichia coli* JDG4 having the highest consumption rate of glutamic acid obtained above by electroporation.

Next, a strain capable of expressing the gene of naphthalene dioxygenase was obtained by an antibiotic screening method, and the selected strain was named as *Escherichia coli* JD938. *Escherichia coli* JD938 was deposited in Leibniz Institute Deutsche Sammlung von Mikroorganismen and Zelkulturen GmbH (DSMZ) of German Collection of Microorganisms and Cell Cultures on Feb. 6, 2019, of which the deposit number was DSM 33021.

Example 2

*Escherichia coli* JD904 was cultured overnight at 37° C. in LB medium.

After that, *Escherichia coli* JD904 was inoculated into an experimental medium or a comparative medium to perform the fermenter culturing.

The composition of the comparative medium is described as follows: yeast extract (YE) 20 g/L, glycerol 50 g/L, tryptophan 5 g/L, isopropyl β-D-1-thiogalactopyranoside (IPTG) 0.5 mM, $CaCl_2$ 1 µM, $MgSO_4$ 1 mM, thiamine 1 mg/L and 1×M9 salt. With regard to the composition of the experimental medium, as compared to the comparative medium, except for 20 g/L of the yeast extract being replaced with 10 g/L of glutamic acid, the remaining ingredients were all the same as those of the comparative medium.

The conditions for the fermenter culturing are described as follows: the temperature for the fermenter culturing is 30° C., the pH value is 7.0, and the dissolved oxygen (D.O.) is 10%.

After 72 hours of culturing, the $OD_{620}$ value of the fermented broth was measured with a spectrophotometer. The measured $OD_{620}$ value was compared to an indigo dye concentration standard curve to obtain an indigo dye concentration (titer of indigo dye) (mg/L).

In addition, 200 mL of the fermented broth was centrifuged and the supernatant was removed to obtain a precipitated bacterial pellet, and then the bacterial pellet was freeze-dried and weighed to determine the dry weight of the cells. The indigo dye content (mg/g of dry weight of the cells) in the cells was calculated by the indigo dye concentration of and the dry weight of the cells.

Figure 1B:
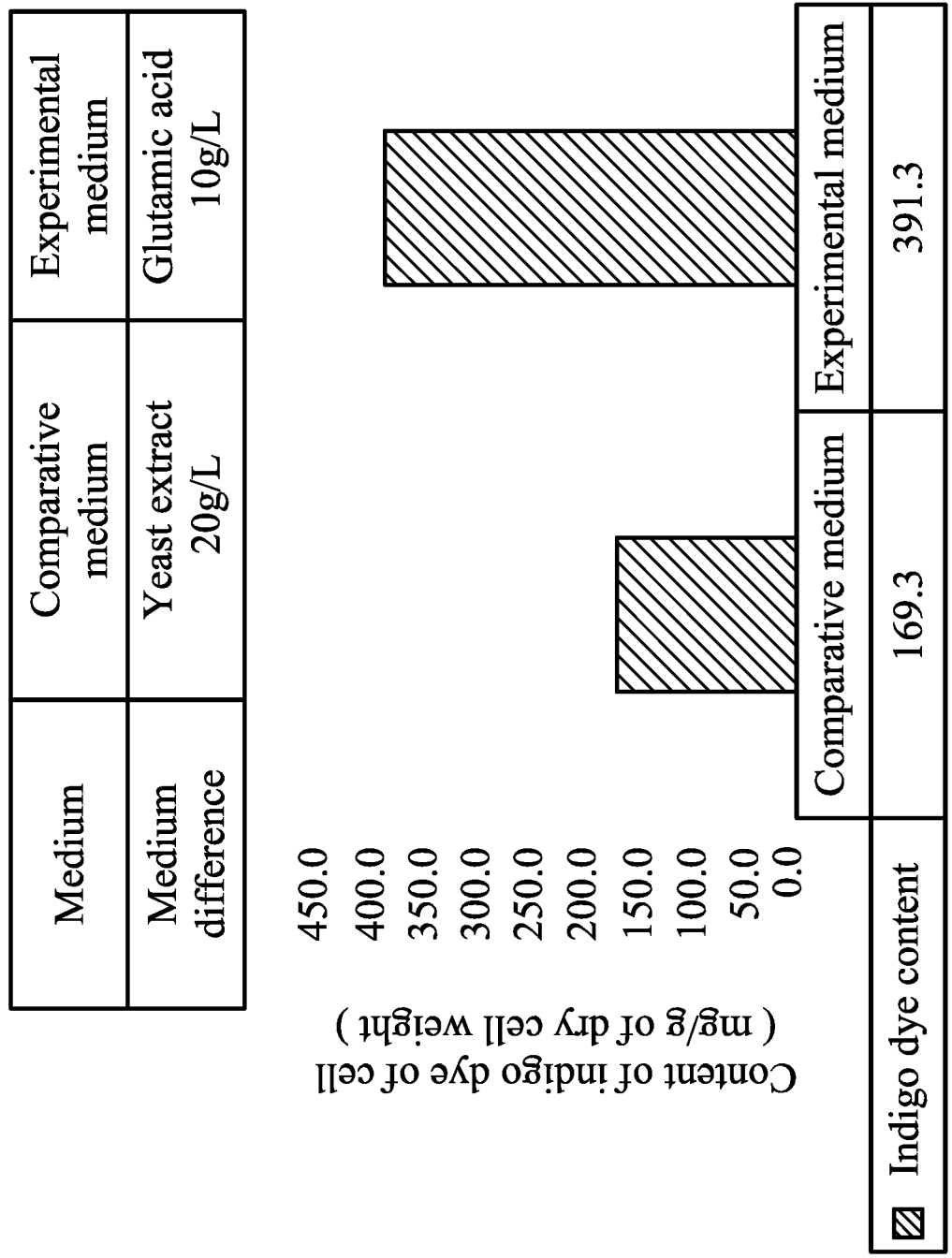
FIG. 1B shows the indigo dye contents in *Escherichia coli* JD904 cultured in an experimental medium (medium with glutamic acid) and a comparative medium (medium without glutamic acid) (mg/g of dry cell weight), respectively.

The results are as shown in FIGS. 1A and 1B.

FIG. 1A and FIG. 1B show that the titer of indigo dye of *Escherichia coli* JD904 cultured in the experimental medium (medium with glutamic acid) is similar to that of *Escherichia coli* JD904 cultured in the comparative medium (medium without glutamic acid), however, the content of indigo dye in *Escherichia coli* JD904 cultured in experimental medium (medium with glutamic acid) is about 2.3 times that in *Escherichia coli* JD904 cultured in the comparative medium (medium without glutamic acid).

Based on the results mentioned above, it is understood that by using a medium with glutamic acid to culture *Escherichia coli*, the purity of the indigo dye produced by *Escherichia coli* can be increased, effectively.

Example 3

*Escherichia coli* JD904 was cultured overnight at 37° C. in LB medium.

After that, *Escherichia coli* JD904 was inoculated into an experimental medium or a comparative medium to perform the fermenter culturing.

The composition of the comparative medium is described as follows: yeast extract (YE) 20 g/L, glycerol 50 g/L, tryptophan 5 g/L, isopropyl β-D-1-thiogalactopyranoside (IPTG) 0.5 mM, $CaCl_2$ 1 µM, $MgSO_4$ 1 mM, thiamine 1 mg/L and 1×M9 salt. With regard to the composition of the experimental medium, as compared to the comparative medium, except for 10 g/L of glutamic acid being additionally added and the yeast extract being adjusted to 1 g/L, the remaining ingredients were all the same as those of the comparative medium.

The conditions for the fermenter culturing are described as follows: the temperature for the fermenter culturing is 30° C., the pH value is 7.0, and the dissolved oxygen (D.O.) is 10%.

After 72 hours of culturing, the $OD_{620}$ value of the fermented broth was measured with a spectrophotometer. The measured $OD_{620}$ value was compared to an indigo dye concentration standard curve to obtain an indigo dye concentration (mg/L).

In addition, 200 mL of the fermented broth was centrifuged and the supernatant was removed to obtain a precipitated bacterial pellet, and then the bacterial pellet was freeze-dried and weighed to determine the dry weight of the cells. The indigo dye content accumulation efficiency (mg/g of dry weight of the cells/hour) in the cells was calculated by the indigo dye concentration of and the dry weight of the cells.

Figure 2A:
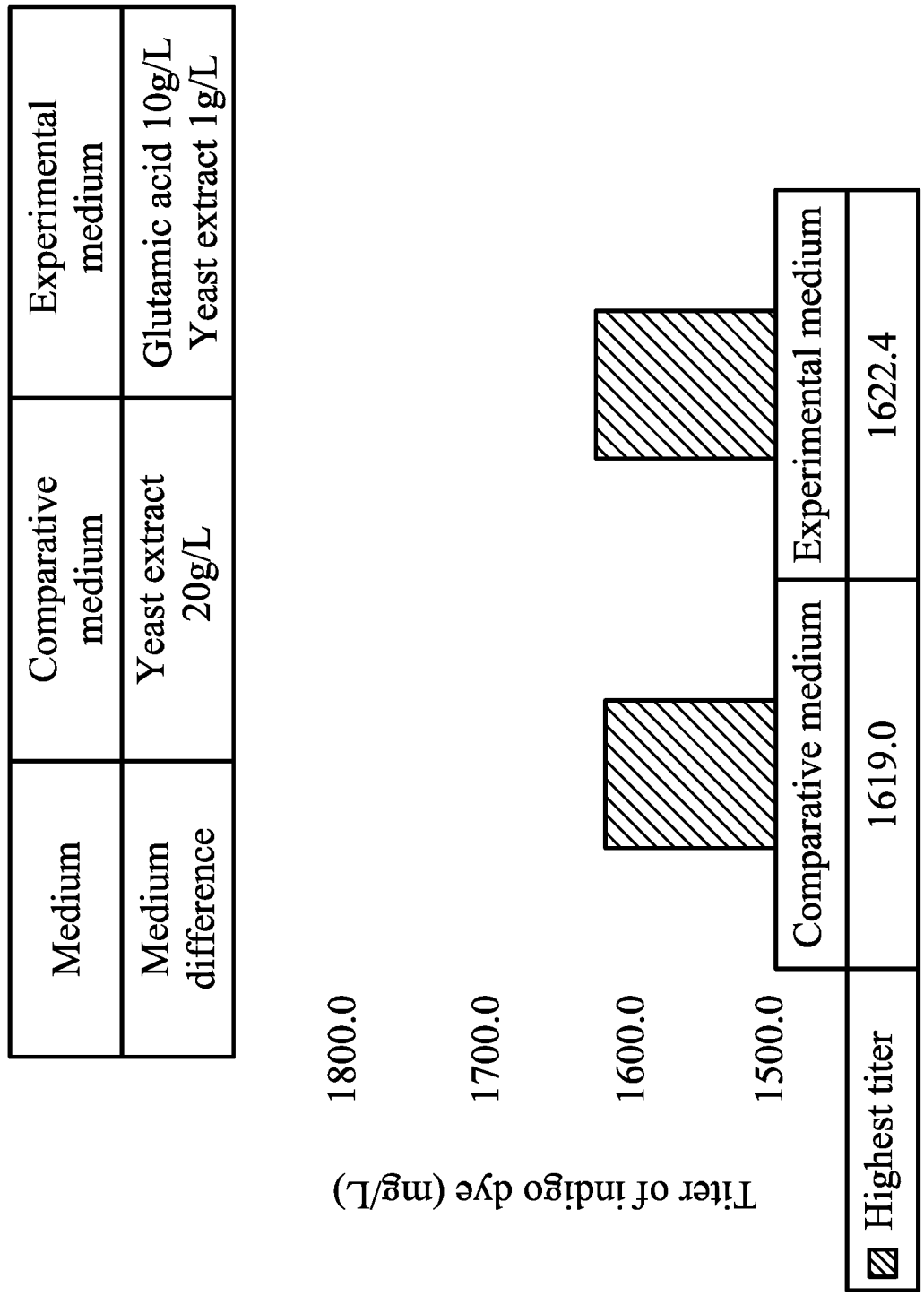
FIG. 2A shows the titers of indigo dye of *Escherichia coli* JD904 cultured in an experimental medium (medium with glutamic acid) and a comparative medium (medium without glutamic acid), respectively.
Figure 2B:
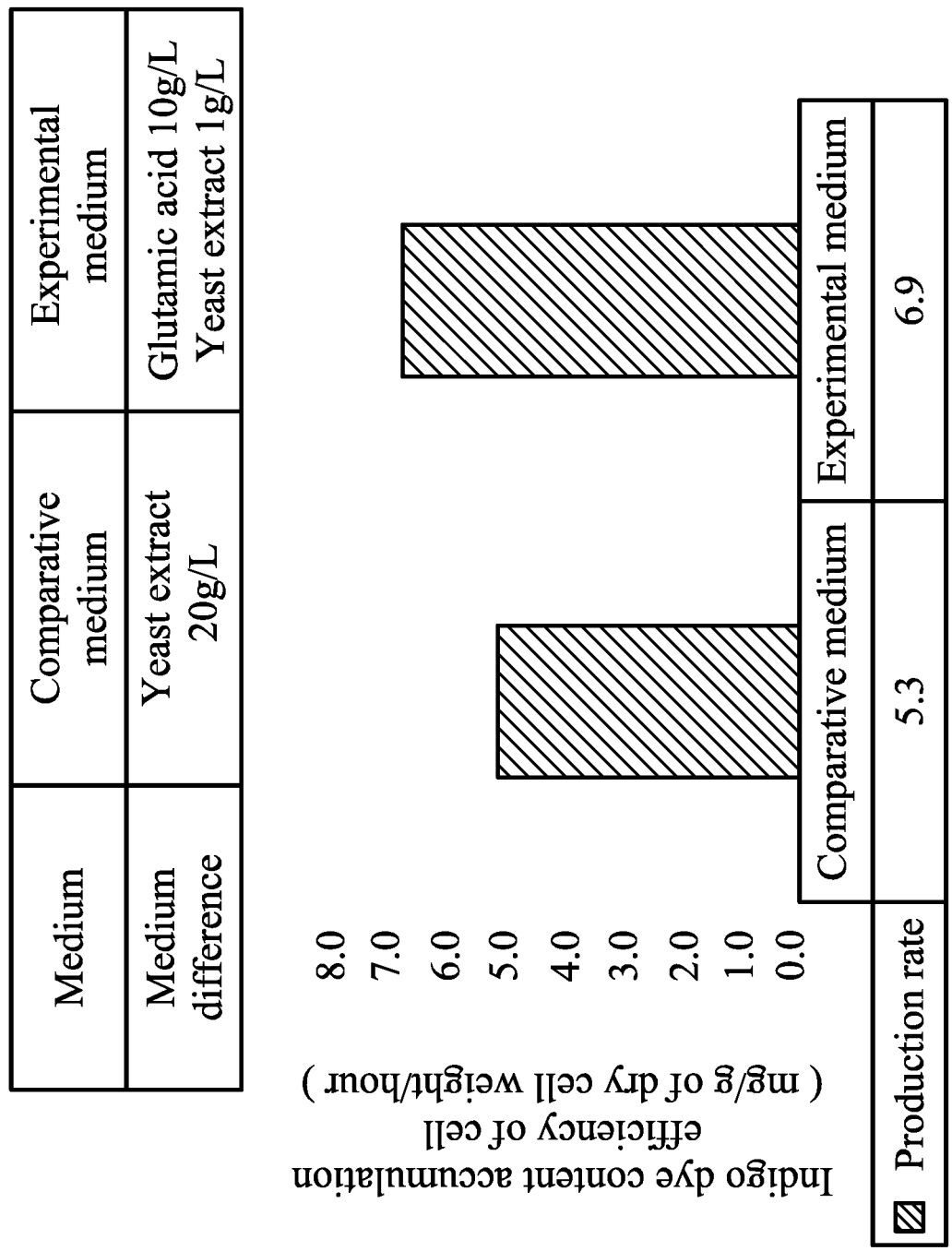
FIG. 2B shows the indigo dye content accumulation efficiency (mg/g of dry cell weight/hour) of *Escherichia coli* JD904 cultured in an experimental medium (medium with glutamic acid) and a comparative medium (medium without glutamic acid), respectively.

The results are as shown in FIGS. 2A and 2B.

FIG. 2A and FIG. 2B show that the titer of indigo dye of *Escherichia coli* JD904 cultured in the experimental medium (medium with glutamic acid) is similar to that of *Escherichia coli* JD904 cultured in the comparative medium (medium without glutamic acid), however, the indigo dye content accumulation efficiency of *Escherichia coli* JD904 cultured in experimental medium (medium with glutamic acid) is about 1.3 times that of *Escherichia coli* JD904 cultured in the comparative medium (medium without glutamic acid).

Based on the results mentioned above, it is understood that by using a medium with glutamic acid to which small amount of yeast extract is added to culture *Escherichia coli*, *Escherichia coli* can produce an indigo dye more rapidly.

Example 4

*Escherichia coli* JD904 and JD938 were separately cultured overnight at 37° C. in LB medium.

Thereafter, *Escherichia coli* JD904 and JD938 were each inoculated into an experimental medium, and cultured in a shake flask at 30° C.

The composition of the experimental medium is described as follows: glutamic acid 10 g/L, glycerol 50 g/L, tryptophan 5 g/L, isopropyl-β-D-thiogalactoside 0.5 mM, $CaCl_2$ 1 µM, $MgSO_4$ 1 mM, thiamine 1 mg/L and 1×M9 salts.

After 24 hours of culturing, the $OD_{600}$ value of the bacterial suspension was measured with a spectrophotometer to determine the growth condition of the bacteria. In addition, 1 mL of the bacterial suspension was centrifuged, and the obtained supernatant was analyzed for the glutamic acid content by YSI biochemical analyzer (model YSI 2700, Wisdom Science) to calculate the glutamic acid consumption of the bacteria.

Figure 3A:
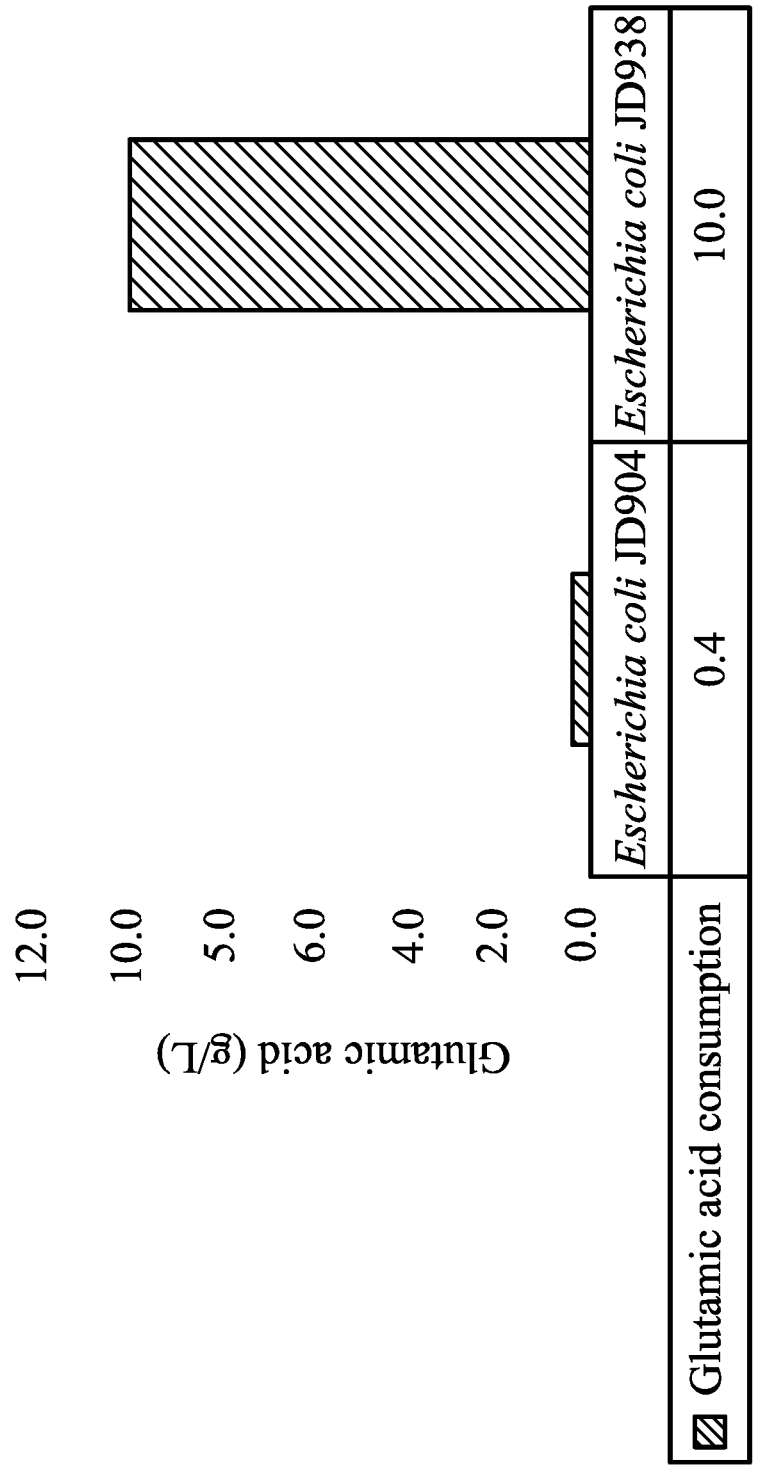
FIG. 3A shows the glutamic acid consumption of *Escherichia coli* JD904 and *Escherichia coli* JD938 cultured in an experimental medium (medium with glutamic acid)
Figure 3B:
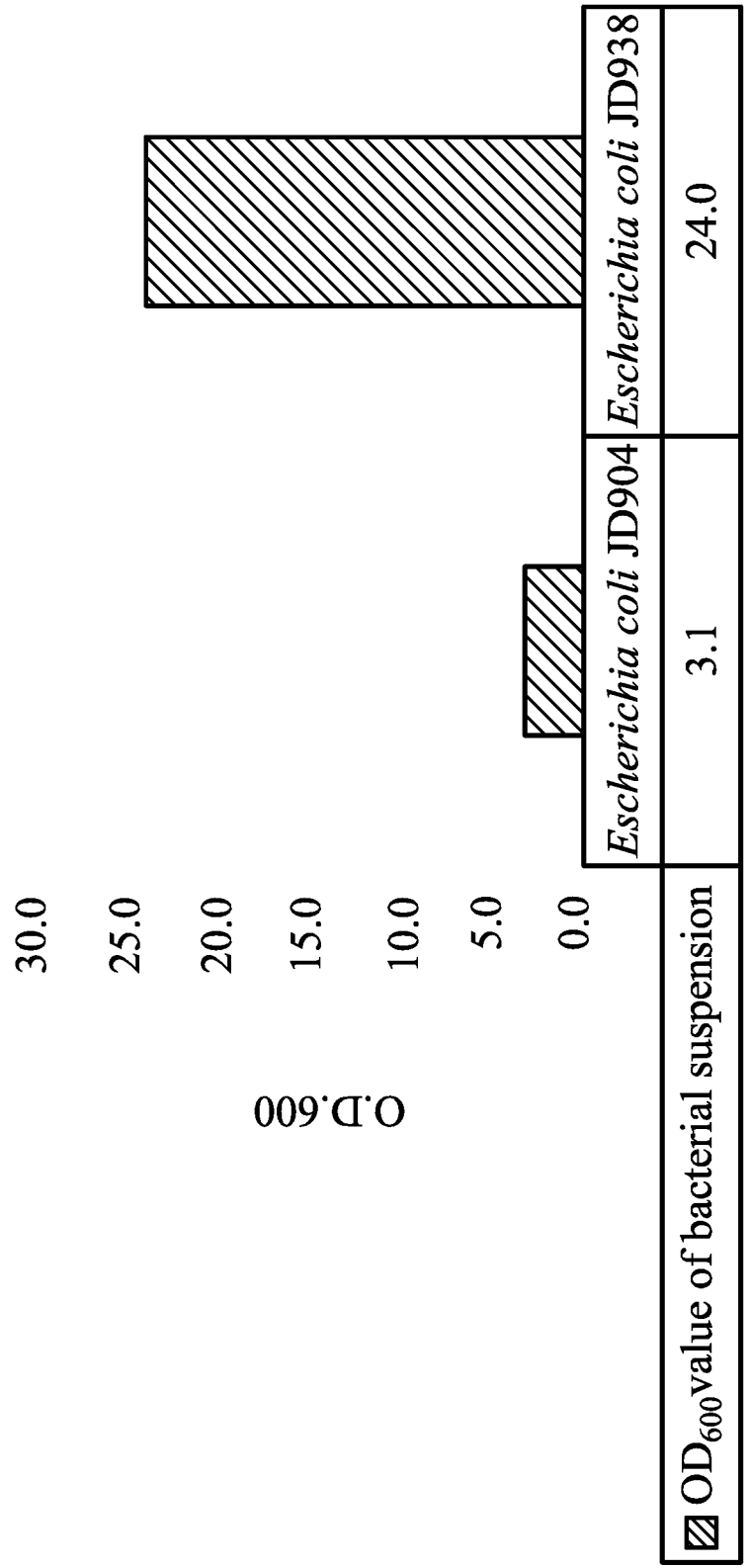
FIG. 3B shows the bacterial growth of *Escherichia coli* JD904 and *Escherichia coli* JD938 cultured in an experimental medium (medium with glutamic acid)

The results are as shown in FIGS. 3A and 3B.

FIGS. 3A and 3B show that the glutamic acid consumption of *Escherichia coli* JD938 is about 20 times that of *Escherichia coli* JD904, and the bacterial concentration of *Escherichia coli* JD938 can be about 8 times that of *Escherichia coli* JD904.

Based on the results mentioned above, it is understood that *Escherichia coli* JD938 can more effectively utilize glutamic acid to grow than *Escherichia coli* JD904.

Example 5

*Escherichia coli* JD904 and JD938 were separately cultured overnight at 37° C. in LB medium.

Thereafter, *Escherichia coli* JD904 and JD938 were each inoculated into an experimental medium, and cultured in a shake flask at 30° C.

The composition of the experimental medium is described as follows: glutamic acid 10 g/L, glycerol 10 g/L, tryptophan 5 g/L, isopropyl-β-D-thiogalactoside 0.5 mM, CaCl$_2$ 1 μM, MgSO$_4$ 1 mM, thiamine 1 mg/L and 1×M9 salts.

After 24 hours of culturing, the cultured medium was centrifuged to obtain a bacterial cell, and then a solvent, dimethyl sulfoxide (DMSO), was added to the bacterial cell and mixed therewith well to obtain an extract. After that, the OD$_{620}$ value of the extract was measured by a spectrophotometer. The measured OD$_{620}$ value was compared to an indigo dye concentration standard curve to obtain an indigo dye concentration (mg/L).

Figure 4:
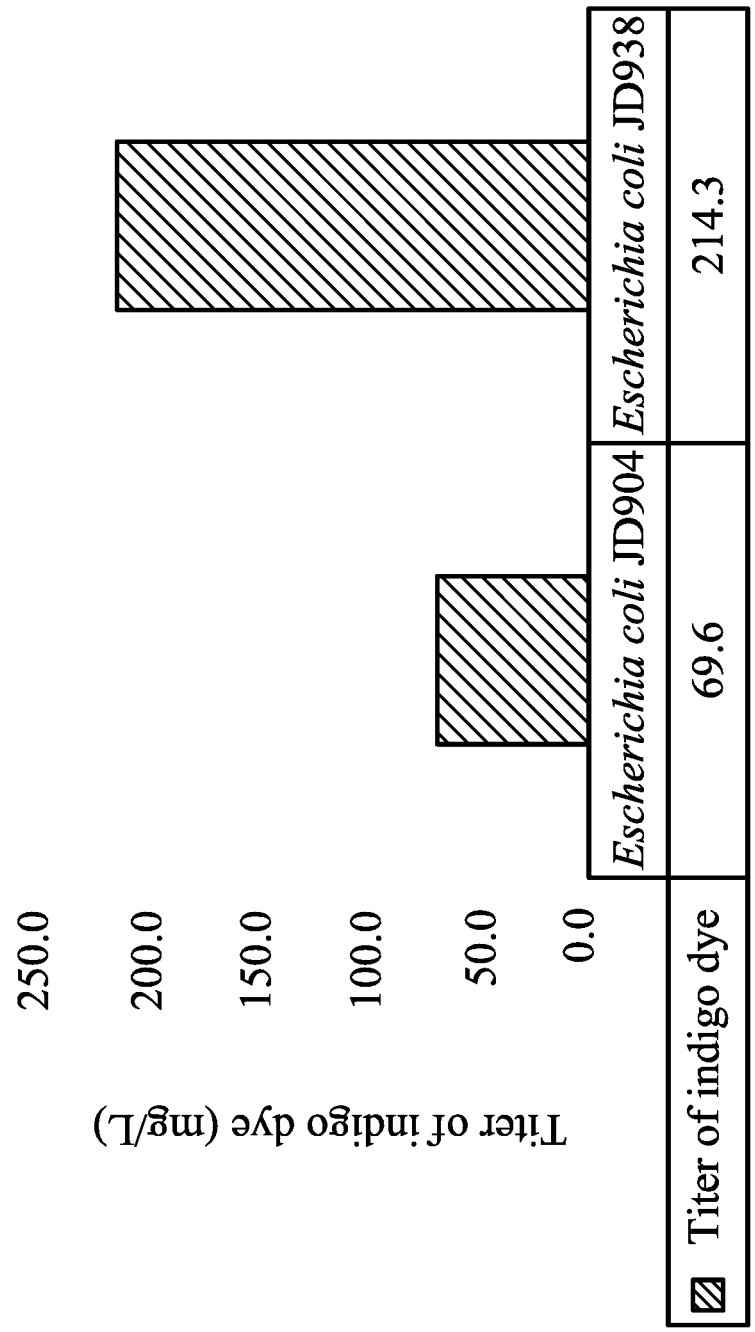
FIG. 4 shows the titers of indigo dye of *Escherichia coli* JD904 and *Escherichia coli* JD938 cultured in an experimental medium (medium with glutamic acid).

The results are as shown in FIG. 4

FIG. 4 shows that the titer of indigo dye of *Escherichia coli* JD938 was more than three times that of *Escherichia coli* JD904.

Based on the results mentioned above, it is understood that *Escherichia coli* JD938 can more efficiently utilize glutamate to grow and improve the efficiency of producing indigo dye compared to *Escherichia coli* JD904.

Example 6

6.1 Test for Glutamic Acid Concentration in Medium

*Escherichia coli* JD904 and JD938 were separately cultured overnight at 37° C. in LB medium.

Thereafter, *Escherichia coli* JD904 and JD938 were each inoculated into an experimental medium, and cultured in a shake flask at 30° C.

The composition of the experimental medium is described as follows: glutamic acid (1 g/L, 5 g/L, 10 g/L, 15 g/L, 20 g/L, 30 g/L or 40 g/L), glycerol (10 g/L), tryptophan (5 g/L), isopropyl-β-D-thiogalactoside (0.5 mM), CaCl$_2$ (1 μM), MgSO$_4$ (1 mM), thiamine (1 mg/L) and 1×M9 salts.

After 24 hours of culturing, the cultured medium was centrifuged to obtain a bacterial cell, and then a solvent, dimethyl sulfoxide (DMSO), was added to the bacterial cell and mixed therewith well to obtain an extract. After that, the OD$_{620}$ value of the extract was measured by a spectrophotometer. The measured OD$_{620}$ value was compared to an indigo dye concentration standard curve to obtain an indigo dye concentration (mg/L).

The results are as shown in Table 4.

TABLE 4

| | Indigo dye production (mg/L) | |
|---|---|---|
| Glutamic acid concentration | JD904 | JD938 |
| 1 g/L | 72.7 | 83 |
| 5 g/L | 72.7 | 185.5 |
| 10 g/L | 68.6 | 246.1 |
| 15 g/L | 67.6 | 213.2 |
| 20 g/L | 60.4 | 212.2 |

TABLE 4-continued

| | Indigo dye production (mg/L) | |
|---|---|---|
| Glutamic acid concentration | JD904 | JD938 |
| 30 g/L | 84 | 105.5 |
| 40 g/L | 76.8 | 91.8 |

The results shown in Table 4 show that *Escherichia coli* JD938 can achieve the highest indigo dye titer when the glutamic acid concentration is about 10 g/L. Moreover, under different glutamic acid concentrations, the titers of indigo dye of *Escherichia coli* JD938 were all higher than that of *Escherichia coli* JD904. According to the results mentioned above, it was understood that a high titer of indigo dye was obtained from *Escherichia coli* JD938 in the condition in which a small amount of glutamic acid was added.

6.2 Test for Concentration of Yeast Extract in Medium

*Escherichia coli* JD904 and JD938 were separately cultured overnight at 37° C. in LB medium.

Thereafter, *Escherichia coli* JD904 and JD938 were each inoculated into an experimental medium, and cultured in a shake flask at 30° C.

The composition of the experimental medium is described as follows: glutamic acid 10 g/L, yeast extract (0 g/L, 1 g/L, 3 g/L or 5 g/L), glycerol (10 g/L), tryptophan (5 g/L), isopropyl-β-D-thiogalactoside (0.5 mM), CaCl$_2$ (1 μM), MgSO$_4$ (1 mM), thiamine (1 mg/L) and 1×M9 salt.

After 24 hours of culturing, the cultured medium was centrifuged to obtain a bacterial cell, and then a solvent, dimethyl sulfoxide (DMSO), was added to the bacterial cell and mixed therewith well to obtain an extract. After that, the OD$_{620}$ value of the extract was measured by a spectrophotometer. The measured OD$_{620}$ value was compared to an indigo dye concentration standard curve to obtain an indigo dye concentration (mg/L).

The results are as shown in Table 5.

TABLE 5

| Strain | JD938 | | | |
|---|---|---|---|---|
| Yeast extract (g/L) | 0 | 1 | 3 | 5 |
| Indigo dye production (mg/L) | 214 | 371 | 251.2 | 185.5 |

According to the results shown in Table 5, it was understood that *Escherichia coli* JD938 can achieve the highest titer of indigo dye by adding a small amount of yeast extract (at a concentration of about 1 g/L).

It will be apparent to those skilled in the art that various modifications and variations can be made to the disclosed embodiments. It is intended that the specification and examples be considered as exemplary only, with the true scope of the disclosure being indicated by the following claims and their equivalents.

What is claimed is:

1. A genetically modified microorganism, comprising:
an exogenous nucleic acid sequence encoding naphthalene dioxygenase (NDO),
wherein the endogenous icd gene of the genetically modified microorganism is knocked out, and the endogenous icd gene encodes isocitrate dehydrogenase (IDH), and
wherein the genetically modified microorganism is capable of using glutamic acid and/or its salts as a nitrogen source to grow and produce indigo dye.

2. The genetically modified microorganism as claimed in claim 1, wherein a source of the genetically modified microorganism comprises a bacterium or a fungus.

3. The genetically modified microorganism as claimed in claim 2, wherein the bacterium comprises a bacterium belonging to the genus *Escherichia*, the genus *Enterobacter*, the genus *Enterococcus*, the genus *Lactobacillus*, the genus *Lactococcus*, the genus *Pseudomonas*, the genus *Citrobacter*, the genus *Corynebacterium*, the genus *Erwinia*, the genus *Klebsiella*, the genus *Morganella*, the genus *Pantoea*, the genus *Pectobacterium*, the genus *Proteus*, the genus *Salmonella*, the genus *Serratia* or the genus *Shigella*.

4. The genetically modified microorganism as claimed in claim 2, wherein the fungus comprises a fungus belonging to the genus *Yarrowia*, the genus *Pichia*, the genus *Rhodotorula*, the genus *Saccharomyces*, the genus *Dekkera*, the genus *Aspergillus*, the genus *Kluyveromyces*, the genus *Penicillium* or the genus *Ustilago*.

5. The genetically modified microorganism as claimed in claim 1, wherein the exogenous nucleic acid sequence comprises a sequence having at least 85% sequence identity to the sequence of SEQ ID NO. 1.

6. A novel genetically modified strain of *Escherichia coli* of which the deposit number is DSM 33021, wherein the endogenous icd gene of the novel genetically modified strain of *Escherichia coli* is knocked out, and the novel genetically modified strain of *Escherichia coli* comprises an exogenous nucleic acid sequence encoding naphthalene dioxygenase.

7. A method for preparing the genetically modified microorganism as claimed in claim 1, comprising the following steps:
(a) knocking out the endogenous icd gene of a microorganism to obtain a icd gene-knockout microorganism;
(b) performing acclimation on the icd gene-knockout microorganism with a medium containing glutamic acid and/or its salts to obtain an acclimatized microorganism; and
(c) introducing an exogenous nucleic acid sequence encoding naphthalene dioxygenase into the acclimatized microorganism to obtain the genetically modified microorganism,
wherein the genetically modified microorganism is capable of using glutamic acid and/or its salts as a nitrogen source to grow and produce indigo dye.

8. The method for preparing a genetically modified microorganism as claimed in claim 7, wherein the microorganism is used to produce indigo dye.

9. The method for preparing a genetically modified microorganism as claimed in claim 7, wherein the microorganism comprises a bacterium or a fungus.

10. The method for preparing a genetically modified microorganism as claimed in claim 7, wherein the exogenous nucleic acid sequence comprises a sequence having at least 85% sequence identity to the sequence of SEQ ID NO. 1.

11. The method for preparing a genetically modified microorganism as claimed in claim 7, wherein the acclimation comprises:
performing a first concentration culturing, and in the first concentration culturing, culturing the icd gene-knockout microorganism with a medium containing a first concentration of glutamic acid and/or its salts to a stationary phase, wherein the first concentration is 0.05-80 g/L.

12. The method for preparing a genetically modified microorganism as claimed in claim 11, wherein the first concentration culturing is performed in 3-6 cycles.

13. The method for preparing a genetically modified microorganism as claimed in claim 11, wherein the icd gene-knockout microorganism is cultured for 12-84 hours to the stationary phase.

14. The method for preparing a genetically modified microorganism as claimed in claim 11, wherein the acclimation further comprises:
   after the first concentration culturing, performing at least one round of an increased concentration culturing, and in each increased concentration culturing, culturing the icd gene-knockout microorganism in a medium containing glutamic acid and/or its salts at a higher concentration than the first concentration to the stationary phase, wherein the concentration of glutamic acid and/or its salts in the medium used for each round of the increased concentration culturing is higher than that of the previous round.

15. The method for preparing a genetically modified microorganism as claimed in claim 14, wherein the increased concentration culturing in each round is performed in about 3-6 cycles.

16. The method for preparing a genetically modified microorganism as claimed in claim 14, wherein the genetically modified microorganism is a genetically modified *Escherichia coli*, and the deposit number thereof is DSM 33021.

17. A method for producing indigo dye, comprising the following steps:
   (a) providing a genetically modified microorganism; and
   (b) culturing the genetically modified microorganism in a medium containing glutamic acid and/or its salts and a precursor of indigo dye to produce indigo dye,
   wherein the genetically modified microorganism comprises the genetically modified microorganism as claimed in claim 1.

18. The method for producing indigo dye as claimed in claim 17, wherein in the medium, the concentration of the precursor of indigo dye is 0.1-25 g/L.

19. The method for producing indigo dye as claimed in claim 17, wherein in the medium, the concentration of the glutamic acid and/or its salts is 0.05-80 g/L.

20. The method for producing indigo dye as claimed in claim 17, wherein the medium further comprises a yeast extract (YE), and the concentration of the yeast extract is 0.05-30 g/L.

* * * * *